US008597626B2

(12) United States Patent
Bui et al.

(10) Patent No.: US 8,597,626 B2
(45) Date of Patent: Dec. 3, 2013

(54) LONG WEAR, WATERPROOF MASCARA COMPOSITION WITH WATER WASHABILITY

(75) Inventors: Hy Si Bui, Piscataway, NJ (US); Mohamed Kanji, Edison, NJ (US); Chunhua Li, Scotch Plains, NJ (US); Bruno Bavouzet, Hoboken, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/825,707

(22) Filed: Jun. 29, 2010

(65) Prior Publication Data

US 2011/0020261 A1 Jan. 27, 2011

Related U.S. Application Data

(60) Provisional application No. 61/221,237, filed on Jun. 29, 2009.

(51) Int. Cl.
*A61K 8/81* (2006.01)
*A61K 8/92* (2006.01)
*A61Q 1/10* (2006.01)
*A61K 8/00* (2006.01)
*A61K 8/18* (2006.01)
*A61Q 5/00* (2006.01)
*A61Q 9/00* (2006.01)

(52) U.S. Cl.
USPC ........................................ 424/70.7; 424/70.1

(58) Field of Classification Search
USPC .............................................. 424/70.1, 70.7
See application file for complete search history.

(56) References Cited

U.S. PATENT DOCUMENTS

| 2,957,838 | A |   | 10/1960 | Mills, Jr. |
| 3,590,076 | A |   | 6/1971 | Heintzelman et al. |
| 3,699,154 | A |   | 10/1972 | Heintzelman et al. |
| 3,933,511 | A |   | 1/1976 | Heintzelman et al. |
| 3,933,512 | A |   | 1/1976 | Heintzelman et al. |
| 4,041,056 | A |   | 8/1977 | Heintzelman et al. |
| 4,226,889 | A |   | 10/1980 | Yuhas |
| 4,420,588 | A |   | 12/1983 | Yoshioka et al. |
| 4,871,536 | A |   | 10/1989 | Arraudeau et al. |
| 5,032,391 | A |   | 7/1991 | Helioff et al. |
| 5,389,363 | A |   | 2/1995 | Snyder et al. |
| 5,618,524 | A |   | 4/1997 | Bolich et al. |
| 5,620,693 | A |   | 4/1997 | Piot et al. |
| 5,800,816 | A |   | 9/1998 | Brieva et al. |
| 5,911,974 | A |   | 6/1999 | Brieva et al. |
| 5,965,112 | A |   | 10/1999 | Brieva et al. |
| 5,985,298 | A |   | 11/1999 | Brieva et al. |
| 5,998,547 | A | * | 12/1999 | Hohner .......................... 525/301 |
| 6,126,929 | A |   | 10/2000 | Mougin |
| 6,274,152 | B1 |   | 8/2001 | Brieva et al. |
| 6,464,964 | B1 |   | 10/2002 | Brieva et al. |
| 6,482,400 | B1 |   | 11/2002 | Collin |
| 6,492,455 | B1 |   | 12/2002 | Nadolsky |
| 6,524,564 | B1 |   | 2/2003 | Kim et al. |
| 6,562,322 | B2 |   | 5/2003 | Brieva et al. |
| 6,716,419 | B2 |   | 4/2004 | Zoltowski et al. |
| 6,780,422 | B2 |   | 8/2004 | Brieva et al. |
| 6,958,148 | B1 |   | 10/2005 | Green et al. |
| 7,005,134 | B2 |   | 2/2006 | Brieva et al. |
| 7,160,550 | B2 |   | 1/2007 | Brieva et al. |
| 7,186,766 | B2 |   | 3/2007 | Harashina et al. |
| 7,314,904 | B2 |   | 1/2008 | Nadolsky et al. |
| 7,423,104 | B2 |   | 9/2008 | Lion |
| 7,682,621 | B2 |   | 3/2010 | Lamberty et al. |
| 7,875,265 | B2 |   | 1/2011 | Blin et al. |
| 8,119,110 | B2 |   | 2/2012 | Blin et al. |
| 2003/0026816 | A1 |   | 2/2003 | Zoltowski et al. |
| 2003/0082218 | A1 |   | 5/2003 | Ichinohe et al. |
| 2003/0147931 | A1 |   | 8/2003 | Brieva et al. |
| 2003/0182734 | A1 |   | 10/2003 | Desenne et al. |
| 2004/0170586 | A1 |   | 9/2004 | Ferrari et al. |
| 2004/0186308 | A1 |   | 9/2004 | Koch et al. |
| 2004/0223986 | A9 |   | 11/2004 | Boussouira et al. |
| 2005/0013992 | A1 |   | 1/2005 | Azad et al. |
| 2005/0180936 | A1 | * | 8/2005 | Pays ........................... 424/70.11 |
| 2005/0220728 | A1 |   | 10/2005 | Kanji et al. |
| 2006/0013840 | A1 |   | 1/2006 | Lamberty et al. |
| 2006/0084764 | A1 |   | 4/2006 | Hanna et al. |
| 2006/0093568 | A1 |   | 5/2006 | Blin et al. |
| 2006/0104940 | A1 |   | 5/2006 | Heinrichs et al. |
| 2006/0110345 | A1 |   | 5/2006 | Lu et al. |
| 2006/0115444 | A1 |   | 6/2006 | Blin et al. |

(Continued)

FOREIGN PATENT DOCUMENTS

DE 100 64 799 A1 6/2002
DE 102004008941 A1 9/2005

(Continued)

OTHER PUBLICATIONS

Hauthal, Tenside Surf. Det. 2008, 45 (1), 30-42 (published: Jan. 2008).*
Vertellus, ZeMac(R) E400 Copolymer Technical Data Sheet, May 29, 2008.*
U.S. Appl. No. 12/825,767, filed Jun. 29, 2010, Bui, et al.
U.S. Appl. No. 12/825,807, filed Jun. 29, 2010, Bui, et al.
U.S. Appl. No. 12/825,587, filed Jun. 29, 2010, Bui, et al.
U.S. Appl. No. 12/825,840, filed Jun. 29, 2010, Bui, et al.
U.S. Appl. No. 12/825,623, filed Jun. 29, 2010, Bui, et al.
U.S. Appl. No. 12/825,726, filed Jun. 29, 2010, Bui, et al.
U.S. Appl. No. 12/825,633, filed Jun. 29, 2010, Bui, et al.
U.S. Appl. No. 12/825,599, filed Jun. 29, 2010, Bui, et al.
U.S. Appl. No. 12/825,816, filed Jun. 29, 2010, Bui, et al.
U.S. Appl. No. 12/825,730, filed Jun. 29, 2010, Bui, et al.
U.S. Appl. No. 12/825,614, filed Jun. 29, 2010, Bui, et al.

(Continued)

*Primary Examiner* — Gina C Justice
*Assistant Examiner* — Genevieve S Alley
(74) *Attorney, Agent, or Firm* — Oblon, Spivak, McClelland, Maier & Neustadt, L.L.P.

(57) ABSTRACT

The present invention is directed to a long wear, washable and waterproof eye makeup composition having a unique texture and feel including (a) at least one sugar silicone surfactant; (b) at least one oil-soluble polar modified polymer; and (c) at least one oil-soluble high carbon polar modified polymer.

17 Claims, No Drawings

(56) References Cited

U.S. PATENT DOCUMENTS

| | | | |
|---|---|---|---|
| 2006/0147396 | A1 | 7/2006 | Monello |
| 2006/0147402 | A1 | 7/2006 | Blin et al. |
| 2006/0159642 | A1 | 7/2006 | Hanna et al. |
| 2006/0165626 | A1 | 7/2006 | Ricard et al. |
| 2006/0188459 | A1* | 8/2006 | Heinrichs et al. ............... 424/63 |
| 2007/0031361 | A1* | 2/2007 | Herrmann et al. ......... 424/70.11 |
| 2007/0092468 | A1 | 4/2007 | Brieva et al. |
| 2007/0110700 | A1 | 5/2007 | Wells et al. |
| 2007/0110702 | A1 | 5/2007 | Ehara |
| 2007/0134181 | A1 | 6/2007 | Shimizu et al. |
| 2007/0212315 | A1 | 9/2007 | Pastor et al. |
| 2007/0256700 | A1 | 11/2007 | Bodelin |
| 2007/0258932 | A1 | 11/2007 | Bui et al. |
| 2007/0259012 | A1 | 11/2007 | Castro et al. |
| 2008/0025934 | A1 | 1/2008 | Lebre et al. |
| 2008/0207871 | A1 | 8/2008 | Seiler et al. |
| 2009/0060959 | A1 | 3/2009 | Igarashi |
| 2009/0130037 | A1 | 5/2009 | Thevenet et al. |
| 2010/0310489 | A1 | 12/2010 | Barba |
| 2010/0330012 | A1 | 12/2010 | Bui et al. |
| 2010/0330015 | A1 | 12/2010 | Bui et al. |
| 2010/0330016 | A1 | 12/2010 | Bui et al. |
| 2010/0330017 | A1 | 12/2010 | Bui et al. |
| 2010/0330022 | A1 | 12/2010 | Bui et al. |
| 2010/0330024 | A1 | 12/2010 | Bui et al. |
| 2011/0020254 | A1 | 1/2011 | Bui et al. |
| 2011/0020255 | A1 | 1/2011 | Bui et al. |
| 2011/0020256 | A1 | 1/2011 | Bui et al. |
| 2011/0020257 | A1 | 1/2011 | Bui et al. |
| 2011/0020260 | A1 | 1/2011 | Bui et al. |
| 2011/0020261 | A1 | 1/2011 | Bui et al. |
| 2011/0020263 | A1 | 1/2011 | Ilekti et al. |
| 2011/0021681 | A1 | 1/2011 | Bui et al. |
| 2011/0021683 | A1 | 1/2011 | Bui et al. |
| 2011/0038819 | A1 | 2/2011 | Bui et al. |
| 2011/0223122 | A1 | 9/2011 | Bui et al. |
| 2011/0223123 | A1 | 9/2011 | Bui et al. |
| 2011/0280817 | A1 | 11/2011 | Ramadan et al. |
| 2011/0280818 | A1 | 11/2011 | Kawaratani et al. |
| 2011/0280820 | A1 | 11/2011 | Bui et al. |
| 2011/0286950 | A1 | 11/2011 | Bui et al. |
| 2011/0286951 | A1 | 11/2011 | Bui et al. |
| 2011/0293550 | A1 | 12/2011 | Bui et al. |
| 2011/0311467 | A1 | 12/2011 | Bui et al. |
| 2012/0004327 | A1 | 1/2012 | Bui et al. |
| 2012/0107263 | A1 | 5/2012 | Bui et al. |
| 2012/0171137 | A1 | 7/2012 | Bradsaw et al. |
| 2012/0171139 | A1 | 7/2012 | Bradshaw et al. |

FOREIGN PATENT DOCUMENTS

| | | | |
|---|---|---|---|
| EP | 1 314 415 A1 | | 5/2003 |
| EP | 1 854 451 A2 | | 11/2007 |
| EP | 2 036 536 A1 | | 3/2009 |
| JP | A-07053921 | | 2/1995 |
| WO | WO 96/03967 A1 | | 2/1996 |
| WO | WO 01/17485 | | 3/2001 |
| WO | WO 02/088456 A1 | | 11/2002 |
| WO | WO 02 098379 A1 | | 12/2002 |
| WO | WO 2006/112690 A1 | | 10/2006 |
| WO | WO 2006/127883 A2 | | 11/2006 |
| WO | WO 2007/048672 A1 | | 5/2007 |
| WO | WO 2007/096400 | * | 8/2007 |
| WO | WO 2007/096400 A1 | | 8/2007 |
| WO | WO 2007/139812 A2 | | 12/2007 |
| WO | WO 2008/046763 | * | 4/2008 |
| WO | WO 2008/046763 A1 | | 4/2008 |
| WO | WO 2009/085888 A1 | | 7/2009 |

OTHER PUBLICATIONS

U.S. Appl. No. 12/825,600, filed Jun. 29, 2010, Bui, et al.
U.S. Appl. No. 12/825,559, filed Jun. 29, 2010, Bui, et al.
U.S. Appl. No. 13/133,176, filed Jun. 7, 2011, Bui, et al.
U.S. Appl. No. 13/133,181, filed Aug. 1, 2011, Bui, et al.
U.S. Appl. No. 13/379,691, Dec. 21, 2011, Bui, et al.
European Office Action Issued Feb. 22, 2013 in Patent Application No. 10 167 788.8.
Hauthal, H. G. Basics, Ingredients, Detergents, Product Safety and Sustainability. Tenside Surf. Det. Jan. 2008, 45 (1), 30-42.
European Search Report dated Mar. 10, 2011, in European Application No. 10167784.7.
European Office Action from European Patent Application No. 10167784.7 dated Mar. 21, 2011 (4 pages).
L. Rudnick, Synthesis, Mineral Oils, and Bio-Based Lubricants, Chemistry and Technology.
Perstorp, Boltorn® H20 product data sheet dated Jan. 3, 2008.
Perstorp, Determination of Viscosity for Bohorn Dendritic Polymers, Aug. 23, 2011.
Mulkern et al. Polymer, 2000, 41 (9), 3193-3203.
Bergbreiter et al. Tetrahedron Letters, 1997, 38 (21), 3703-3706.
European Search Report issued Apr. 8. 2011, in European Patent Application No. 10167791.2 (with English Abstract).
European Search Report issued Mar. 21, 2011, in European Application No. 10167792.0.
European Search Report issued Apr. 6, 2011, in European Patent Application No. 10167794.6.
European Search Report dated Mar. 14, 2011, issued in European Application No. 10167785.4.
European Patent Office Communication dated Apr. 18, 2011, issued in European Application No. 10167785.4.
European Search Report issued Mar. 10, 2011, in European Application No. 10167790.4.
European Office Action issued in European Patent Application No. 10167790.4 dated Mar. 21, 2011 (4 pages).
International Search Report issued May 20, 2010 in PCT/US09/067332 filed Dec. 9, 2009.
International Search Report issued Aug. 11, 2010 in PCT/US09/68246 filed Dec. 16, 2009.
International Search Report Issued Jul. 26, 2010 in PCT/US09/068151 filed Dec. 16, 2009.
International Search Report issued Jul. 28, 2010 in PCT/US09/68251 filed Dec. 16, 2009.
International Search Report issued Jul. 30, 2010 in PCT/US09/68148 filed Dec. 16, 2009.
http://www.Chemical Book.com/ChemicalProductProperty_EN_CB3748204.htm, Poly (methyl vinyl ether-alt-maleic anhydride), 2010.
International Search Report Issued Jul. 30, 2010 in PCT/US09/068146 filed Dec. 16, 2009.
International Search Report issued Jul. 23, 2010 in PCT/US09/68245 filed Dec. 16, 2009.
Extended European Search Report Issued Nov. 29, 2012 in Patent Application No. 08867867.7.
International Search Report issued May 31, 2010 in PCT/US09/067338 filed Dec. 9, 2009.

* cited by examiner

LONG WEAR, WATERPROOF MASCARA COMPOSITION WITH WATER WASHABILITY

CROSS-REFERENCE TO RELATED APPLICATIONS

This application claims the benefit of priority from U.S. Provisional Application Ser. No. 61/221,237, filed Jun. 29, 2009, the entire contents of which are hereby incorporated by reference.

FIELD OF THE INVENTION

The present invention generally relates to a novel mascara composition and method of making-up eyes. More particularly, the present invention relates to a mascara composition which is long-wear, waterproof and washable which, until now, could only be achieved through the use of latex film formers.

BACKGROUND OF THE INVENTION

It is well known in the industry that one way of making a mascara composition which is both waterproof and long wear is to make it anhydrous. Thus, the composition will typically comprise volatile solvents and film forming polymers. This type of composition, however, is not washable with water.

Conventional mascara compositions which are both washable and long wear, but not waterproof, require the use of latex film formers in combination with an oil-in-water emulsion.

The use of latex film formers to form such mascara compositions has numerous drawbacks. First, latex film formers are somewhat expensive and require large amounts thereof to be used, adding to the cost of the finished goods. Secondly, latex film formers can be difficult to formulate with due to the large solid content load required, thus making them unstable, as is, or sensitive to added ingredients.

Therefore, it is desirable to provide an eye makeup composition which is waterproof, long wear, washable and has a unique gel-like texture and feel, without the need for having to use latex film formers or surfactants/emulsifiers.

BRIEF SUMMARY OF THE INVENTION

A first aspect of the present invention is directed to an eye makeup composition that includes: (a) at least one sugar silicone surfactant; (b) at least one oil-soluble polar modified polymer; and (c) at least one oil-soluble high carbon polar modified polymer.

A second aspect of the present invention is directed to a method of making up eyes involving applying the above-disclosed composition onto the eyes.

It has been surprisingly found that a composition according to an embodiment of the present invention is shiny, water and smudge resistant, and has enhanced water washability and texture.

DETAILED DESCRIPTION OF THE INVENTION

Other than in the operating examples, or where otherwise indicated, all numbers expressing quantities of ingredients and/or reaction conditions are to be understood as being modified in all instances by the term "about".

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Keratinous substrates", as used herein, include but are not limited to, skin, hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 250 C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 370 C., 400 C., 450 C., 500 C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C. "Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

Sugar Silicone Surfactant

According to the present invention, compositions comprising at least one sugar silicone surfactant are provided. The sugar silicone surfactant of the present invention has the following formula:

Sach-X-Dn-X-Sach where Sach represents a saccharide moiety containing multiple hydroxyl groups. Suitable saccharide moieties include, but are not limited to, those based on monosaccharides such as, for example, glucose, fructose, galactose, ribose, mannose, sorbose, etc., and those based one oligosaccharides such as, for example, sucrose, lactose, palatinose, raffinose, lactosucrose, glucosylsucrose, galactosyl-sucrose, xylobiose, etc. Preferably, the saccharide moiety is based on a monosaccharide, most preferably glucose;

X represents a linear or branched, saturated or unsaturated, C1 to C40 hydrocarbon-based group, possibly containing in their chain one or more oxygen, sulphur and/or nitrogen atoms. Preferably, X represents a linear, unsubstituted alkyl group containing at least one N atom, most preferably a linear, unsubstituted alkyl group having 1-6 carbon atoms and at least one N atom;

D represents a silicone based group of the formula R2SiO, where R2 represents a linear or branched, saturated or unsaturated, C1 to C10 hydrocarbon-based group. Preferably, R2 is an unsubstituted C1 to C3 alkyl group (methyl, ethyl, propyl), most preferably a methyl group; and n represents a number between 1 and 1000, preferably between 100 and 500, more preferably between 250 and 400, and more preferably between 300 and 350, including all ranges and subranges therebetween.

Preferably, such sugar silicone surfactants are prepared by reacting a lactone form of the saccharide with an amino form of the D group, thereby forming an alkyl group X having an N atom between the saccharide moiety and the silicone moiety.

Particularly preferred sugar silicone surfactants include gluconamidoethylaminopropylsilicone, lactobionolactonesiloxane, or a mixture thereof.

Preferably, the sugar silicone surfactant represents from about 0.5% to about 25% of the total weight of the composition, more preferably from about 0.75% to about 15% of the total weight of the composition, and most preferably from about 1% to about 10%, including all ranges and subranges therebetween.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA." "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720] also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil soluble polar modified polymer(s) represent from about 1% to about 30% of the total weight of the composition, more preferably from about 2.5% to about 15% of the total weight of the composition, and most preferably from about 5% to about 10%, including all ranges and subranges therebetween.

Oil-Soluble High Carbon Polar Modified Polymer

According to the present invention, compositions comprising at least one oil-soluble high carbon polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the Lico-Care name having designations such as CM 401, which is a maleic anhydride modified wax having a Mw of 2025 and a crystallinilty of 11%, C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the oil-soluble high carbon polar modified polymer(s) represent from about 1% to about 20% of the total weight of the composition, more preferably from about 3% to about 17% of the total weight of the composition, and most preferably from about 5% to about 15%, including all ranges and subranges therebetween.

According to the present invention, the polar modified polymers are interacted with the sugar silicone surfactant compound. Without intending to be bound by theory, it is believed that the reason for this is that due to the physical interactions which take place when the polar modified polymers are combined with the sugar silicone, the subsequent formulation that is formed is surprisingly and unexpectedly able to entrap large amounts of water molecules within its matrix. The resultant formulation is eminently capable of forming a film, is self-emulsifying, waterproof, and inherently possesses the desired smooth texture and feel. Moreover, the product is both stable and capable of carrying various types of ingredients.

Optional Ingredients

Water

According to preferred embodiments, the composition of the present invention may also contain water. Water, if present, is typically present in an amount of from about 5% to about 50% by weight, such as from about 10% to about 40% by weight, such as from about 25% to about 35% by weight, all weights based on the total weight of the composition, including all ranges and subranges therebetween. Preferably, sufficient water is present to provide an emulsion, preferably a water-in-oil emulsion.

Non-Volatile Solvent

The cosmetic composition of the present invention can optionally further comprise at least one non-volatile oil solvent. As used herein, the term "non-volatile" means having a boiling point of greater than about 100 degrees C. The at least one non-volatile solvent typically comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula R5COOR6 in which R5 represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with R6 +R7 ≥10, such as, for example, Purcellin oil (cetostearyl octanoate), isononyl isononanoate, C12 to C15 alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

C8 to C26 fatty alcohols, for instance oleyl alcohol; and mixtures thereof.

The non-volatile, if present, is preferably present in the cosmetic composition of the invention in an amount of from about 0.5% to about 15% by weight, such as from about 1% to about 10% by weight, such as from about 2% to about 5% by weight, all weights based on the total weight of the composition.

Volatile Solvent

The composition of the present invention can also include at least one volatile solvent chosen from a volatile silicone oil or a volatile non-silicone oil.

Suitable volatile silicone oils include, but are not limited to, linear or cyclic silicone oils having a viscosity at room temperature less than or equal to 6cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |
| PDMS DC 200 (3 St) from Dow Corning | 102 | 3 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, and for example, the oils sold under the trade names of Isopar or Permethyl, the C8 to C16 branched esters such as isohexyl or isodecyl neopentanoate and their mixtures. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

In general, the at least one volatile solvent, if present, is present in the composition in an amount of from about 5% to about 80% by weight, such as from about 10% to about 60% by weight, and from about 20% to about 40% by weight, all weights based on the total weight of the composition, including all ranges and subranges therebetween.

The composition of the present invention may also include other ingredients. Examples thereof include, but are not limited to, colorants such as pigments and dyestuffs, co-solvents, waxes, plasticizers, preservatives, fillers, active ingredients, film formers and sunscreens.

It has surprisingly been discovered that the composition of the present invention forms a stable, waterproof emulsion, having a unique texture and feel, without the need for having to employ a surfactant/emulsifier to form the emulsion. Without intending to be bound by theory, it is believed that the combination of the sugar silicone surfactant and polar modified polymer forms a matrix capable of entrapping large amounts of water molecules within its hydrophobic matrix. Since water is entrapped within the hydrophobic matrix, the composition provides excellent water-resistant, long wear properties when applied on eyelashes and/or eyebrows. When a user washes the composition from the eyes, the water entrapped within the matrix is released, thereby allowing the composition to be easily removed from the eyelashes and/or eyebrows. The composition is washable with water without the need for having to employ conventional latex film forming polymers.

In addition, the composition also exhibits unique creamy and smooth texture, and enhanced shine.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

A cosmetic composition was prepared containing the below-disclosed ingredients.

| Phase | Component | Example 1 |
| --- | --- | --- |
| A | Caprylic/capric Triglyceride | 1.0 |
| A | Propylene-ethylene-Maleic Anhydride Copolymer | 8.0 |

-continued

| Phase | Component | Example 1 |
|---|---|---|
| A | C26-C28 Alpha Olefin Maleic Acid Anhydride | 6.0 |
| A | Isohexadecane | 2.66 |
| A | Iron Oxides | 8.0 |
| A | Isododecane | 30.59 |
| A | Propylparaben | 0.2 |
| B | DI Water | 17.00 |
| B | Disodium EDTA | 0.1 |
| B | Potassium Cetyl Phosphate | 2.00 |
| B | Methylparaben | 0.25 |
| B | Pentylene Glycol | 2.00 |
| B | NaOH | 1.00 |
| B | Gluconamidoethylaminopropylsilocone (and) Alcohol | 20.00 |
| C | Simethicone | 0.1 |
| D | Phenoxyethanol (and) Methylparaben (and) Isopropylparaben (and) Isobutylparaben (and) Butylparaben | 1.1 |
| | Total | 100 |

Procedure:

In the main beaker A, the following were added: Isododecane, Caprylic/capric Triglyceride, Polypropylene-ethylene-Maleic Anhydride Copolymer wax, C26-C28 Alpha Olefin Maleic Acid Anhydride, Propylparaben. The contents were then heated to 90° C. until all the solids melted.

Added Iron Oxides into main beaker and started homogenizing the batch for 1 h at 850 RPM. (Temperature was maintained at 85-90° C.)

In another beaker B, added deionized water, Disodium EDTA, Potassium Cetyl Phosphate, Methylparaben, Pentylene Glycol, Sugar Silicone (Gluconamidoethylaminopropylsilocone and Alcohol) and NaOH. These were mixed until uniform and then heated to 90° C.

Slowly added contents of beaker B to beaker A. Then added Simethicone to the mixture. Mixed for 20 minutes at 500 RPM.

Changed to sweep blade and started cooling using 50 RPM.

At 35° C., added a mixture of Phenoxyethanol (and) Methylparaben (and) Isopropylparaben (and) Isobutylparaben (and) Butylparaben.

Continued cooling to 25° C.

What is claimed is:

1. A composition, comprising:
   (a) a surfactant system comprising at least one sugar silicone surfactant;
   (b) an oil phase comprising at least one oil, at least one oil-soluble polar modified polymer, wherein the oil-soluble polar modified polymer consists of polypropylene and/or polyetheylene monomers, and maleic anhydride units, and has a weight-average molecular weight of less than or equal to 25 000 g/mol and a melting point above 75° C., and
   at least one oil-soluble high carbon polar modified polymer, wherein the oil-soluble high carbon polar modified polymer consists of C26-C28 monomers, and maleic anhydride units, and has a weight-average molecular weight of less than or equal to 30000 g/mol and a crystallinity of 8% to 60%; and
   (c) water,
   wherein the composition is in the form of an emulsion.

2. The composition of claim 1, wherein the sugar silicone surfactant is gluconamidoethylaminopropylsilicone.

3. The composition of claim 1, wherein the sugar silicone surfactant is present in an amount of from about 0.5% to about 25% by weight, based on the weight of the composition.

4. The composition of claim 1, wherein the oil-soluble polar modified polymer is present in an amount of from about 1% to about 30% by weight, based on the weight of the composition.

5. The composition of claim 1, wherein the oil-soluble high carbon polar modified polymer is present in an amount of from about 1% to about 20% by weight, based on the weight of the composition.

6. The composition of claim 1, wherein water is present in an amount of from about 5% to about 50% by weight, based on the weight of the composition.

7. The composition of claim 1, wherein the oil phase comprises at least one non-volatile oil.

8. The composition of claim 7, wherein the non-volatile oil is present in an amount of from about 0.5% to about 15% by weight, based on the weight of the composition.

9. The composition of claim 1, wherein the oil phase comprises at least one non-volatile oil present in an amount of from about 5% to about 80% by weight, based on the weight of the composition.

10. The composition of claim 1, further comprising at least one colorant.

11. The composition of claim 1, further comprising at least one wax.

12. A method of making-up eyelashes comprising applying onto the eyelashes a composition comprising:
   (a) a surfactant system comprising at least one sugar silicone surfactant;
   (b) an oil phase comprising at least one oil, at least one oil-soluble polar modified polymer, wherein the oil-soluble polar modified polymer consists of polypropylene and/or polyetheylene monomers, and maleic anhydride units, and has a weight-average molecular weight of less than or equal to 25 000 g/mol and a melting point above 75° C., and
   at least one oil-soluble high carbon polar modified polymer, wherein the oil-soluble high carbon polar modified polymer consists of C26-C28 monomers, and maleic anhydride units, and has a weight-average molecular weight of less than or equal to 30000 g/mol and a crystallinity of 8% to 60%; and
   (c) water,
   wherein the composition is in the form of an emulsion.

13. The composition of claim 1, wherein the oil-soluble polar modified polymer has from about 0.5% to about 10% maleic anhydride units.

14. The composition of claim 1, wherein the oil-soluble high carbon polar modified polymer has from about 5% to about 30% maleic anhydride units.

15. The composition of claim 1, wherein the surfactant system consists essentially of the at least one silicone sugar surfactant.

16. The composition of claim 1, wherein the composition comprises a matrix formed by (a) the at least one sugar silicone surfactant and (b) the oil-soluble polar modified polymer and/or the oil-soluble high carbon polar modified polymer.

17. The composition of claim 16, wherein water is entrapped within the matrix.

* * * * *